United States Patent [19]

Kinoshita et al.

[11] Patent Number: 5,762,929
[45] Date of Patent: Jun. 9, 1998

[54] ANTI-MOTONEURON-DISEASE AGENT

[75] Inventors: Masao Kinoshita; Yasuo Iwasaki; Ken Ikeda; Toshiya Shiojima; Nozomu Tagaya; Tomoko Kobayashi, all of Tokyo, Japan

[73] Assignee: SAM Research Corporation, Japan

[21] Appl. No.: 508,952

[22] Filed: Jul. 31, 1995

[30] Foreign Application Priority Data

Jan. 31, 1995 [JP] Japan ................................. 7-036211

[51] Int. Cl.$^6$ .......................... A61K 38/44; A61K 38/54
[52] U.S. Cl. .............................. 424/94.4; 424/94.3
[58] Field of Search ........................ 424/94.4, 94.3

[56] References Cited

U.S. PATENT DOCUMENTS

| 5,109,118 | 4/1992 | Mizushima | 424/85.8 |
| 5,238,837 | 8/1993 | Inoue et al. | 435/189 |
| 5,277,908 | 1/1994 | Beckman et al. | 424/94.4 |
| 5,310,958 | 5/1994 | Mizushima | 554/41 |
| 5,336,493 | 8/1994 | Poznansky et al. | 424/94.2 |
| 5,362,491 | 11/1994 | Mizushima | 424/180.1 |
| 5,366,729 | 11/1994 | Marklund et al. | 424/94.4 |

FOREIGN PATENT DOCUMENTS

| WO94/06428 | 3/1994 | WIPO | A61K 31/47 |
| WO 94/19493 | 9/1994 | WIPO | C12Q 1/68 |

OTHER PUBLICATIONS

M. Tagaya et al., "Recombinant Human Superoxide Dismutase Can Attenuate Ischemic Neuronal Damage in Gerbils" Pergamon Press Ltd. (1992).

D. Truelove et al., "Neuronal Protection with Superoxide Dismutase in Repetitive Forebrain Ischemia in Gerbils" *Free Radical Biology & Medicine* 17(5):445–450 (1994).

K. Kitagawa et al., "Free Radical Generation During Brief Period of Cerebral Ischemia May Trigger Delayed Neuronal Death" *Neuroscience* 35(3):551–558 (1990).

T. Maysuyama et al., "Effects of Recombinant Superoxide Dismutase on Manganese Superoxide Dismutase Gene Expression in Gerbil Hippocampus After Ischemia" *Stroke* 25(7)1417–1423 (1994).

S. Zeman et al., "Excitatory Amino Acids, Free Radicals and the Pathogenesis of Motor Neuron Disease" *Neuropathology and Applied Neurobiology* 20:219–2331 (1994).

M. Sendtner et al., "Oxidative Stress and Motorneuron Disease" *Current Biology* 4(11):1036 (1994).

*Primary Examiner*—Theodore J. Criares
*Attorney, Agent, or Firm*—Testa, Hurwitz & Thibeault, LLP

[57] ABSTRACT

The present invention relates to an novel anti-motoneuron-disease agent, comprising superoxide dismutase conjugated with lecithin through chemical crosslinking represented in the following generic formula (PC-SOD) as an effective ingredient:

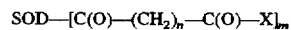

$$SOD-[C(O)-(CH_2)_n-C(O)-X]_m$$

wherein SOD represents superoxide dismutase and X represents a residue of lysolecithin having a hydroxy group at position 2 of glycerol whose hydrogen atom of the hydroxyl group at position 2 is removed.

A pharmaceutical agent of the present invention may improve symptoms of motoneuron diseases such as amyotrophic lateral sclerosis etc. by oral or parenteral administration. The present invention also relates to a novel treatment method for motoneuron disease by administrating PC-SOD and novel use of PC-SOD as a medical composition for preparing an agent for treating motoneuron disease.

18 Claims, 7 Drawing Sheets

VEHICLE

PC-SOD
($10^5$ U/kg)

ANTI-MOTONEURON-DISEASE AGENT

FIELD OF THE INVENTION

The present invention relates to a novel medicinal and medical use of lecithinized superoxide dismutase. More specifically, it relates to an anti-motoneuron-disease agent comprising lecithinized superoxide dismutase an an effective ingredient, a method for treating motoneuron diseases which comprises administrating lecithinized superoxide dismutase and use of medical composition which comprises lecithinized superoxide dismulase for preparing an agent for treating motoneuron disease.

BACKGROUND OF THE INVENTION

Superoxide dismutase (hereinafter, may be abbreviated as SOD) is widely distributed in a living body of animals, plants or microorganisms and is known as an enzyme which degrades active oxygen, that is, superoxide anion radical.

In a pharmaceutical aspect, it is expected to be applied to the treatment of various kinds of inflammation, such as in rheumatism, myocardial infarction or organ transplantation, or for removal of radioals occuring after usage of antithrombotic agents.

In another aspect, it is investigated for the application to gastric mucous membrane disorder and expected to be beneficial. (Research on lipoperoxide(kasanka-shishitsu kenkyu), vol. 16, 74p (1992))

SOD is readily excreted to urine when it is administered intravenously, because it has low cellular affinity and its half life in blood is said to be only 4–6 minutes. In order to increase its half life in blood, modification of SOD with ficoll, polyethyleneglycol, rat albumin, dextran etc., have been tried.

However, SOD modified with ficoll or polyethyleneglycol showed extremely lowered enzymic activity and low cellular affinity.

Further, SOD modified with rat albumin was reported to have antigenicity.

In addition, it was reported that modification of SOD with dextran augmented antiinflammatory action of SOD, but that it did not suppress immunogenicity. Recently, it was reported that a biologically active protein such as SOD was chemically modified with lecithin (phosphatidylcholine, hereinafter, may be abbreviated as PC), where it was described that PC bound modified biologically active protein had higher cellular affinity than that of unmodified one and its tissue distribution was significantly different from that of unmodified one. It was also described that such modification was expected to augment pharmacological activity of the biologically active protein, decrease its adverse effect and stimulate its absorption. Further, phosphatidylcholinized SOD (hereinafter, may be abbreviated as PC-SOD) showed stimulative effect on the treatment of inflammation by burn. (Japan laid-open patent publication (kokai)-3-163100; Japan laid-open patent publication (kokai) 3-170438; U.S. Pat. No. 5,109,118-specification)

Further, it was described to be useful as an antiinflammatory agent without adverse effect such as antigenicity. In Japan laid-open patent publication (kokal)-6-54681, it was described about the effect on respiratory resistance induced by Forssman antiserum.

In addition, the report was made on the effect of PC-SOD on ulcerous gastrointestinal injury.

Recently, it was also reported that SOD coordinated with Cu and Zn (hereinafter, may be abbreviated as Cu/Zn SOD) suppressed free radical-induced neural disorders in vitro (Lipton S. A., et al., Nature, vol.364, 626–632p (1993)) and in vivo (Cadet J. L., et al., J. Neurochem. vol.62, 380–383p (1994); Epstein C. J., et al., Gene Transfer and Therapy in the Nervous System (eds Gage, F. and Christen, Y). Berlin, Springer-Verlag, 106–117 (1992); Muizelaar J. P., et al., J. Neurosurg. vol.78, 375–382p (1993)).

Further, it was recently reported (Rosen D. R., et al., Nature, vol.362, 59–62p (1993)) that mutation of Cu/Zn SOD was found in a patient with familial amyotrophic lateral sclerosis (Louis Cehrig disease. Hereinafter, amyotrophic lateral sclerosis may be abbreviated as ALS). In addition, it was also reported that there are an excessive oxidation, decreased Cu/Zn SOD activity and oxidative damages of protein in familial or sporadic ALS (Bowling A. C., et al., J. Neurochem. vol.61, 2322–2325p (1993); Robberecht W., et al., J. Neurochem. vol.62, 384–387p (1994)). ALS is a typical motoneuron disease in which selective lesion is observed in motoneuron.

Motoneuron disease is a generic name of diseases where only voluntary movement nervous system is selectively impaired, sensory nerve and autonomic nerve are healthy and the other visceral nervous system is not invaded. Motoneuron disease is degenerative neurotic disease which having a strong tendency to progress to worse, and at present, no radical therapy has been found to cure any of these motoneuron diseases. Onset of typical ALS is observed after middle age and the feature of the disease is characterized by starting with amyotrophy in limb distal muscle, followed by progressive systemic amyotrophy in several years, and eventually to bulbar palsy, but without any invasion in orbicular muscle of eye nor in sphincter muscle of urethrae even at the final stage of the disease. The prognosis is terribly bad and there is not any therapy to cure the diseases at present, which leads to death of the patient by worsening bulbar palsy within 5 years. Though it is possible to lengthen life span by using artificial respiratory apparatus, it is not an eredicative therapy. Therefore, pharmaceutical agents are eagerly desired for the treatment of the diseases. In WO94/06428 and WO94/19493, medicinal use of SOD in diseases such as ALS etc. was described.

Usage of SOD polypeptides was described on the basis of the results of the experiment using cultured nerve cell (WO94/06428) and on the basis of the results that the mutation of SOD caused familial ALS (WO94/19493).

However, any pharmacological effect of SOD on ALS was not confirmed by in vivo experiment using model animals in the above two. In addition, even if SOD is administered in vivo, its half life is short and its sufficient pharmacological effect can not be expected. Therefore, usage of SOD, as a therapeutic agent, in a treatment method by administration and as a medical composition for preparing an agent for motoneuron disease such as ALS needs a big breakthrough.

From the view point of the above, the present inventors have investigated the application of PC-SOD as a therapeutic agent for the treatment of motoneuron disease using wobbler mice which is a model animal of motoneuron disease (Ikeda, K., et al., Ann. Neurol. vol.30, 304p (1993); Mitsumoto H.,et al., Ann. Neurol. vol.36, 142–148p (1994); Mitsumoto H.,et al., Science, vol.265, 1107–1110p (1994)), found that it improved the symptoms of motoneuron disease and, then, accomplished the present invention.

SUMMARY OF THE INVENTION

A object of the present invention is to supply an anti-motoneuron-disease agent, comprising superoxide dismutase conjugated with lecithin through chemical crosslinking as an effective ingredient. Another object of the invention is to supply a method for treating motoneuron disease in mammals which comprises administrating to a mammal in need of such treatment therapeutically effective amount of the superoxide dismutase conjugated to lecithin through chemical crosslinking and use or a medical composition which comprises superoxide dismutase conjugated to lecithin through chemical crosslinking, for preparing an agent for treating motoneuron disease.

DETAILED DESCRIPTION OF THE PREFERRED EMBODIMENTS

<1> PC-SOD used in the present invention

The term "lecithin" in the present invention and present specification includes lysolecithin.

PC-SOD as an effective ingredients of pharmaceutical agent of the present invention can be usually obtained by conjugating more than one lecithin derivatives, wherein chemical crosslinking agent is bound to the residue of lysolecithin, with SOD. This PC-SOD is represented in the following formula(1):

$$SOD—[C(O)—(CH_2)_n—C(O)—X]_m \qquad (1)$$

X in the above formula(1) represents a residue of lysolecithin having a hydroxy group at position 2 of glycerol whose hydrogen atom of the hydroxyl group at position 2 is removed.

X is represented in the following formula(2):

$$—O—CH(CH_2OR)[CH_2OP(O)(O^-)(OCH_2CH_2N^+(CH_3)_3)] \qquad (2)$$

R in the above formula(2) represents a fatty acid residue (acyl group), preferably, $C_{10}$–$C_{28}$ saturated or unsaturated fatty acid residue and, more preferably, $C_{14}$–$C_{22}$ saturated fatty acid residue such as myristoyl group, palmitoyl group, stearoyl group and others.

A palmitoyl group having 16 carbon atoms is especially preferred as a saturated fatty acid residue.

Further, —C(O)—(CH$_2$)$_n$—C(O)— represents a residue of chemical crosslinking agent. This residue of chemical crosslinking agent may be a residue that both hydroxyl groups (portion corresponding to hydroxyl groups of dicarboxylic acid in the case of a reactive derivative) of a linear dicarboxylic acid represented as HO—C(O)—(CH$_2$)$_n$—C(O)—OH, an anhydride thereof, an ester thereof, a halide thereof or the other reactive derivatives of dicarboxylic acids was removed.

These are used to bind SOD with lecithin and generically named as chemical crosslinking in the present invention and present specification. The chemical crosslinking in the above formula(1) conjugated with one end of the aforementioned lysolecitin residue through an ester bond.

And the other end of this chemical crosslinking was estimated to bind directly with amino group of SOD through amide bond. In this formula, —(CH$_2$)$_n$— represents bivalent group which is derived from a linear alkane by removing a hydrogen atom from carbon atoms of the both ends thereof, wherein n represents a integral number more than 2, preferably n is 2–10, and especially preferable n is 3.

The m in the aforementioned formula(1) represents the average number of lecithin bound with one molecule of SOD through chemical crosslinking, wherein m is an integral number more than 1, preferably m is 1–16 and especially preferable m is 4.

SOD represented in the aforementioned formula(1) is not especially restricted, but from the view point of using as a pharmaceutical agent in human being and considering its immunogenicity, SOD derived from human is preferable, human derived Cu/Zn SOD (hereinafter, may be abbreviated as human Cu/Zn SOD) is most preferable.

As human Cu/Zn SOD, naturally occuring human Cu/Zn SOD prepared from human tissue or recombinant Cu/Zn SOD whose amino acid sequence is substantially the same as that of naturally occuring human Cu/Zn SOD can be used.

In addition, a mutated human Cu/Zn SOD where cystein at position 111 is replaced with serine by site-specific point mutation (Japan laid-open patent (kokai) 62-130684) and a chemically modified human Cu/Zn SOD where cystein at position 111 is chemically modified (Japan laid-open patent publication (kokai) 6-199895) can be also used, but human Cu/Zn SOD where cystein at position 111 is chemically modified to, for example, S-(2-hydroxyethylthio) cystein has a uniform charge and molecular weight, and its SOD activity is stable. Therefore, this chemically modified human Cu/Zn SOD can be preferably used.

Conjugation of lecithin derivatives with SOD can be performed by the method described in Japan laid open patent publication (kokai) 6-54681, and, thereby, PC-SOD can be prepared. The detail will be described in a preparation example.

<2> A Pharmaceutical Agent, Treatment Method and use of a Medical Composition of the Present Invention The aforementioned PC-SOD can be widely used an an anti-motoneuron-disease agent, treatment method for motoneuron disease and use of a medical composition for preparing an agent for treating motoneuron disease. The anti-motoneuron-disease agent and treatment method may be used in amyotrophic lateral sclerosis (ALS), spinal progressive muscular atrophy, familial spastic paralysis, Charcot-Marie-Tooth disease, progressive bulbar palsy, juvenile muscular atrophy of unilateral upper extremity (Hirayama disease), etc., especially preferably used in ALS. The anti-motoneuron-disease agents (comprising PC-SOD) and treatment method (by administrating PC-SOD) of the present invention have an improving action in these diseases and the symptoms.

On the present invention, PC-SOD can be administrated orally and parenterally by injection (intramuscular, subcutaneous, intradermal, intravenous and so on), per oral, inhalation and other administration methods. The pharmaceutical agents can be prepared appropriately according to administration method. Dosage form may include injections (solutions, suspensions, emulsions, solids soluble at use, etc.), tablets, capsules, granules, powders, liquids, lipofication agent, gels, ectal powders, spraies, inhalation powders, suppositories.

On the pharmaceutical preparation, conventional ingredients usually used for pharmaceutical agents, such as, oxoipients, binders, lubricants, coloring agents, disintegrants, etc. can be used. On the present invention, PC-SOD can be used in combination with other anti-motoneuron-disease agents, so far as they will not affect the activity of PC-SOD.

Effective dosage of the PC-SOD may be estimated 100 U/kg-10000 U/kg for clinical use, considering the effective dosage in wobbler mice in the examples of the present invention. But it is not limited thereto, because it depends on the degree of disorder or the body weight of patients.

"One unit" in the present specification represents the amount of the PC-SOD with which the reduction rate of cytochrome c is inhibited to 50% when determined by oytochrome c method (xanthine—xanthine oxidase-cytochrome c system) at pH 7.8 and at 30° C.

The pharmaceutical agents of the present invention comprising PC-SOD as an effective ingredient can be used as an anti-motoneuron-disease agent, because it is clear from the results of the examples mentioned below that the present agents have an action of improving the symptoms in motoneuron disease, such as amyotrophic lateral sclerosis and so on. The treatment method for motoneuron disease by administrating PC-SOD and use of PC-SOD as a medical composition for preparing an agent for treating motoneuron disease are also useful according to the same reason.

The present invention is further described in detail in the following preparation example of PC-SOD used in the present invention and other examples, but the scope of the present invention is not restricted by those examples:

PREPARATION EXAMPLE

<1> Preparation of human Cu/Zn SOD derivative (Cu/Zn -coordinated human superoxide dismutase, wherein elusion acid at position 111 is S-(2-hydronyethylthio)cystein)

Said SOD was prepared by the method described in Japan laid-open patent (kokai)6-199895 as follows:

E.coli 545πHR (pHT351) (FERMP-9435) was cultivated, followed by disruption of the cultured cell body to yield crude extract of human SOD. To this crude extract solution, ammonium sulfate was added. Obtained precipitate was purified through Q-Sepherose FF (produced by Pharmacia) column and by another ammonium sulfate precipitation. The filtrate through 0.2 µm filter was lyophilized to yield colorless solid (recombinant human apo-SOD). The recombinant human apo-SOD was dissolved in 10 mM triethanolamine buffer solution (pH 7.0), and bis(2-hydroxyethyl)disulfide was added to the solution. The solution was again adjusted to pH 7.0 and stirred at 4° C. for 24 hours. NaCl, 2M acetic acid buffer solution (pH 5.0) and aqueous solution of 1M $CuCl_2$ were added to the solution, and stirred at 4° C. for 13 hours. Then, the solution was adjusted at pH 7.0, followed by ammonium sulfate precipitation (4° C., 100% saturation), and the precipitate was collected. The precipitate was dissolved in 10 mM triethanolamine buffer solution (pH 7.0) and desalted by dialysing against 10 mM triethanolamine buffer solution (pH7.0). This fraction was applied to a Q-Sepharose FF (produced by Pharmacia) column, followed by stepwise elution with 5 mM, 10 mM, 20 mM, and 50 mM NaCl, and SOD fraction was collected. To the SOD fraction, ammonium sulfate was added (4° C., 100% saturation) and the precipitate was collected. The precipitate was dissolved in water to make an aqueous solution, followed by dialysing the solution against 0.5M NaCl aqueous solution and, then, water. The dialyzed solution was lyophilized to yield human SOD derivative. The amino acid at position 111 of this human SOD derivative is S-(2-hydroxyethylthio)cystein.

<2> Preparation of PC-SOD

PC-SOD was prepared by the method described in Japan laid-open patent (kokai) 6-54681 as follows:

(1) Synthesis of an active ester of 2-(4-hydroxycarbonylbutyroyl)lysolecithin (1-1) Synthesis of 2-(4-hydroxycarbonylbutyroyl) lysolecithin To a suspension of lysolecithin having hydroxy group at position 2 of glycerol in chloroform and pyridine (80 ml/20 ml), DMAP(N,N-dimethylaminopyridine) and glutaric anhydride were added, followed by stirring at 60° C. for 15 hours. Then, the reaction mixture was concentrated under vacuum, and the residue was dissolved in a solution of chloroform:methanol;water=4:5:1 and applied to an ion-exchange column (Dowex 50W-X8, produced by Dow Chemical) equilibrated with the same solution. Followed by TLC analysis, fractions containing the object compound were collected. After the concentration of the solvent under vacuum, the residue was purified by a column packed with ODS (octadecylsilane) to yield the object compound.

(1-2) Synthesis of an active ester of 2-(4-hydroxycarbonyl-butyroyl)lysolecithin The carboxylic acid obtained in (1-1) was dissolved in dichloromethane and cooled to 0° C., to which N-hydroxysuccinimide and, then, tetrazol were added. And DCC(1,3-dicyclohexylcarbodiimide) dissolved in dichloromethane was slowly addded, and stirring at room temperature for 15 hours. The insoluble substance was removed from the reaction solution by filtration with Celite to yield a dichloromethane solution of active ester.

(2) Synthesis of PC-SOD in which 4 lecithin derivatives on the average bind with 1 molecule of SOD SOD prepared in preparation example <1> was dissolved in 50 mM borate buffer solution (pH8.5) and reacted with the active ester synthesized in the aforementioned (1) which amount is 0.8 time in mole ratio to the whole amino groups of SOD by the following method:

Dichloromethane of active ester solution was removed and the residue was dissolved in DMF(N,N-dimethylformamide), and the solution was added to 50 mM borate buffer (pH 8.5). SOD was dissolved in 50 mM borate buffer solution (pH 8.5), followed by the filtration. To the SOD solution, DMF was added up to 50 and cooled to 0° C. To this solution of SOD, DMF solution of the active ester was droped.

The reaction mixture was stirred at 0° C. for 15 hours and filtrated.

The filtrate was applied to a gel filtration column packed with Sephacryl S-300 (produced by Pharmacia), eluted with the same buffer as the above reaction buffer solution and PC-SOD eluted fractions were collected, followed by purification through ion-exchange chromatography and concentration by ultrafiltration. The protein concentration was determined by Lowry method (Lowry, O. H. et al., J. Biol. Chem., vol.193, 260p (1951)) and unreacted amino groups of SOD were analysed by TNBS method (trinitrobenzene sulfonate, Goodwin, J. F., et al., Clin. Chem., vol. 16, 24P (1970)). The number of bound lecithin derivatives per one molecule of SOD was 4.0 on the average from the above analytical results.

Thus obtained PC-SOD in a transparent blue green or green solution, and its pH was 7–8. The molecular weight of monomer of PC-SOD subunit (PC-SOD is a homodimer of the subunit) was determined by SDS-polyacrylamide gel electrophoresis to be about 18000.

EXAMPLE 1

Toxicological and pharmacological tests of PC-SOD (concentration, 30 mg/ml; specific activity, $3.07 \times 10^3$ U/protein-mg) prepared in the aforementioned preparation example were carried out. PC-SOD was dissolved in 5% mannitol aqueous solution to give the solution with final concentration of 5 mg/ml (hereinafter, abbreviated as PC-SOD solution), and which was used for the above tests. This PC SOD solution was a colorless to light bluegreen transparent solution and its pH was 6–8. The osmotic pressure ratio of the solution against physiological saline solution was about 1.

<Acute Toxicity Test>

(1) Acute toxicity test in rat

PC-SOD solution was administered at the dosage of 100 mg/kg into tall vein of female and male SD rats (n=b respectively). During 14 days after the administration, general conditions, mortality and body weight of the animals warp observed. On the 15th day, the autopsy and morphological examination of the animals were carried out. As a result, the lethal dose of PC-SOD in the case of intravenous administration was estimated to be more than 100 mg/kg, because there were no dead animals and no toxic sign with regard to general conditions, body weight and morphological examination after autopsy was observed.

(2) Acute toxicity test in monkey

PC-SOD solution was administered at the dosage of 100 mg/kg into limb vein of 2 female monkeys. During 14 days after the administration, general conditions, mortality and body weight of the animals were observed. As a result, the lethal dose of PC-SOD in the case of intravenous administration was estimated to be more than 100 mg/kg, because there were no dead animals, and no toxic sign with regard to general conditions and body weight.

<Pharmacological Test>

Following the initial diagnosis of motoneuron disease symptom (forelimb atrophy) at 3–4 weeks after birth, ten wobbler mice per group (each n=10) were administered in a blind manner either PC-SOD or a vehicle solution daily to carry out pharmacological tests described below. The groups used were as follows:

(A) A group of mice received intraperitoneally 5% mannitol aqueous solution daily (hereinafter, referred to as non-treated group)

(B) A group of mice received into intraperitoneally $10^4$ U/kg of PC-SOD solution daily (hereinafter, referred to as L-SOD group)

(C) A group of mice received intraperitoneally $10^5$ U/kg of PC-SOD solution daily (hereinafter, referred to as H-SOD group)

(1) Suppression of deformity of forelimb

Figure 8:
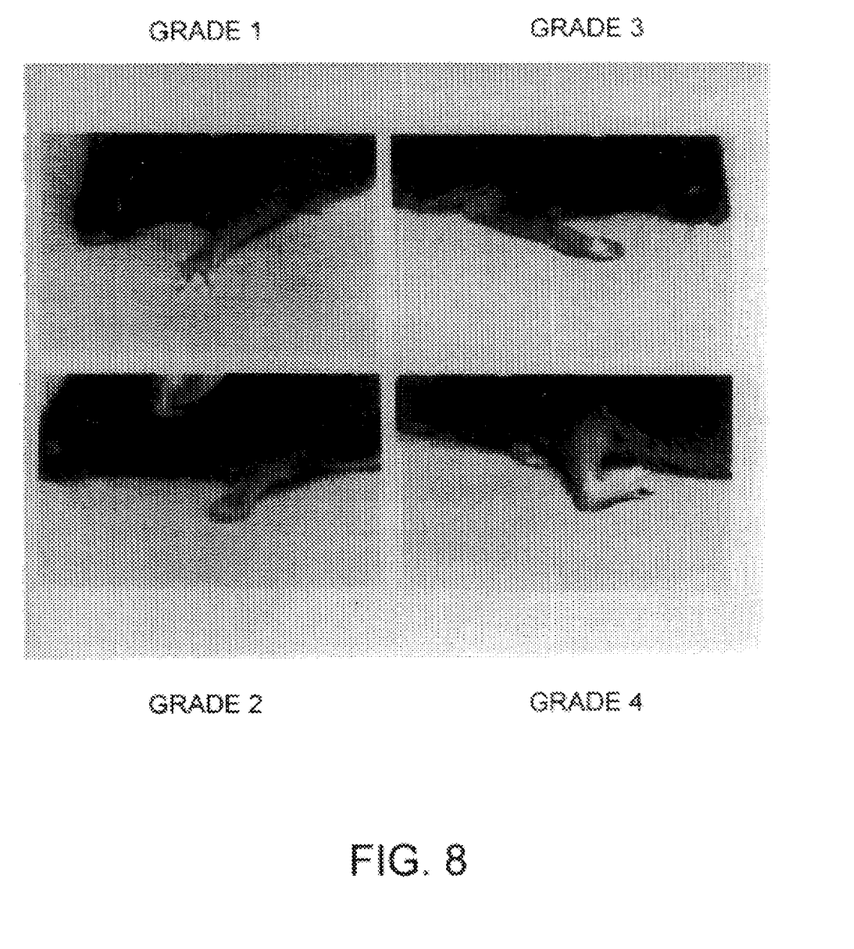
FIG. 8 shows the grades of deformity of forelimbs in wobbler mice (photograph of morphology of organism).

Paw deformity was examined before, at 2 weeks after and at 4 weeks after the initial administration of PC-SOD in the non-treated group, in the L-SOD group and in the H-SOD group. Paw deformity was scored as the following. The deformity progresses from grade 1 to grade 4 in wobbler mice:

grade 1: paw atrophy grade 2: curled digits grade 3: curled wrists grade 4: forelimb flexed to chest Typical example of these grades are shown in photos (FIG. 8)

Figure 1:
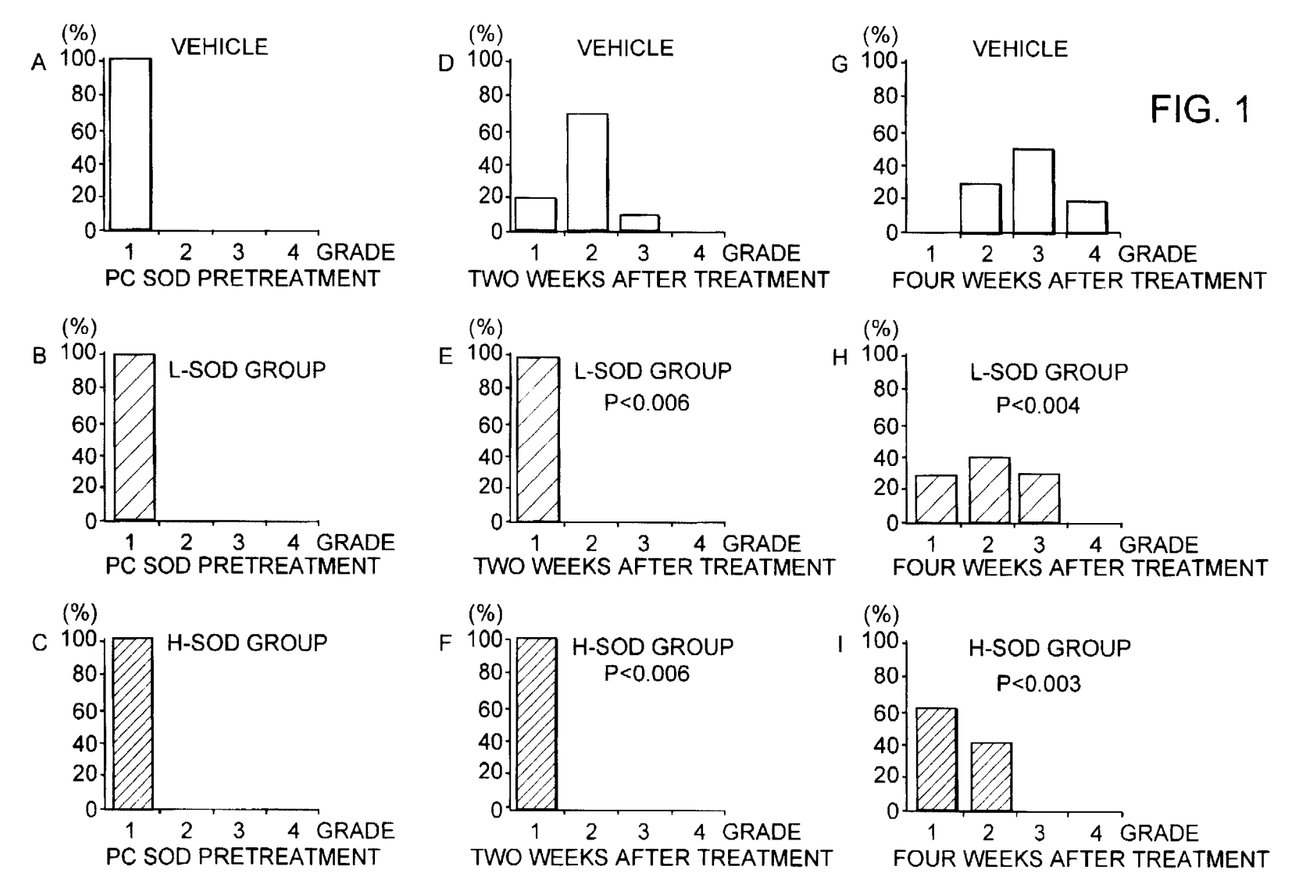
FIG. 1 shows the progression of forelimb deformity in wobbler mice prior to PC-SOD administration (A,B,C), at 2 weeks after the initial administration (D,E,F), at 4 weeks after the initial administration (G,H,I). A, D and G are the result in non-treated group, B,E and H are the result in L-SOD group, C,F and I are result in H-SOD group. The horizontal axis represents the grade of forelimb deformity and the vertical axis represents the number of mice (percentage to the whole). And the value showed in p< represents level of significant difference compared to the non-treated group.

Statistical significance was analyzed by the Wilcoxon rank-sum test. The results are shown in FIG. 1.

The grade of forelimb deformity did not differ among three groups before the imitation of PC-SOD, but the progression of deformity in the L-SOD group and the H-SOD group both of which received PC-SOD was significantly suppressed in comparison with that in the non-treated group ($p<0.006$ in the L-SOD group and $p<0.006$ in the H-SOD group at 2 weeks after; $p<0.004$ in the L-SOD group and $p<0.003$ in the H-SOD group at 4 weeks after). It was suggested that PC-SOD would suppress the progression of deformity in wobbler mice in a dose dependent manner, because the progression of deformity in the H-SOD group was suppressed much more than that in the L-SOD group.

(2) Suppression of reduction of grip strength

The maximum muscle strength in the forelimbs was measured before, at 1 week after, at 2 weeks after, at 3 weeks after and at 4 weeks after the initial administration PC-SOD in the non-treated group, in the L-SOD group and in the H-SOD group. It was carried out making the mice grasp a horizontal wire gauge connected to a special dynamometer with both front pews and keep themselves in the air.

Figure 2:
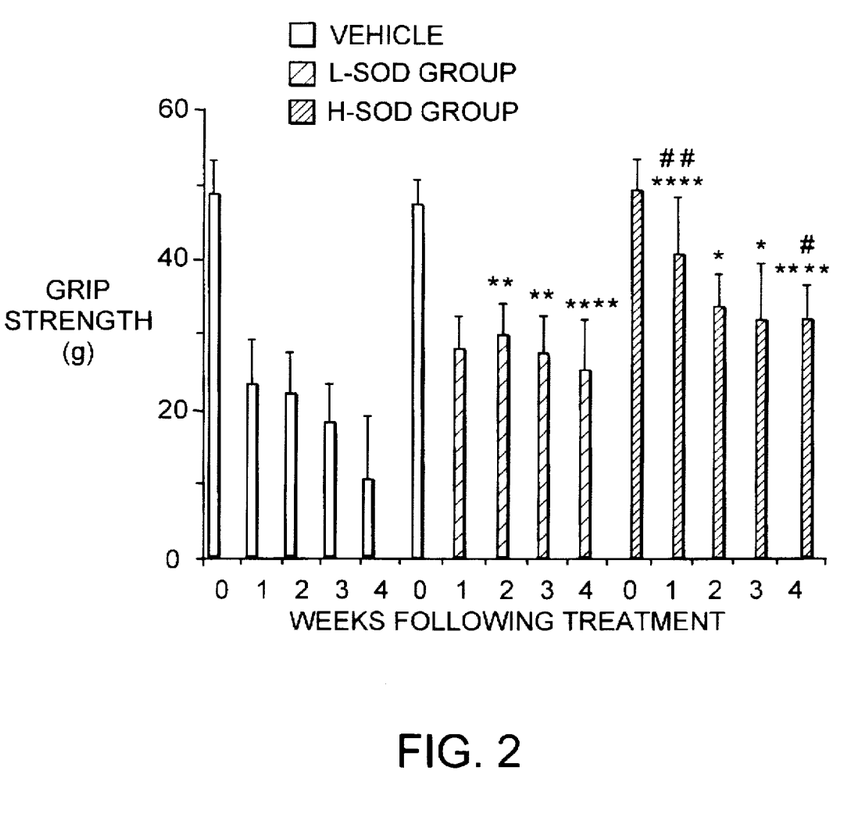
FIG. 2 shows grip strength at 1–4 weeks after the initial administration of PC-SOD in the non-treated group, the L-SOD group and H-SOD group. The horizontal axis represents weeks after initial adminstration and the vertical axis represents grip strength (g). Further, *, , or ** in the figure means that there was a significant difference with a level of p<0.003, p<0.002 or p<0.001 respectively, compared to the non-treated group. In addition, # or ## in the figure means that there was a significant difference with a level of p<0.04 and p<0.007 respectively, compared to the L-SOD group.

Statistical significance was examined by the paired Student's t-test. The results are shown in FIG. 2.

As a result, the reduction of grip strength in the L-SOD group and in the H-SOD group was significantly suppressed in comparison with that in the non-treated group (in the L-SOD group, $p<0.002$ at 2 weeks and 3 weeks, $p<0.001$ weeks after the initial administration; in the H-SOD group, p<0.001 at 1 week and 4 weeks, p<0.003 at 2 weeks and 3 weeks after the initial administration).

In addition, the reduction ratio of grip strength ([(grip strength at 4 week after the initial administration of PC-SOD/grip strength prior to the administration of PC-SOD)-1]×100(%)) in the non-treated group was −78.0+1.8% (mean±standard deviation (S.D.) %), while that in the L-SOD group was −46.9+14.8%.

The results of non-parametric Wilcoxon signed rank test showed that reduction ratio of grip strength in the L-SOD group was significantly suppressed with p<0.006, compared to that in the non-treated group. Further, reduction rate or grip strength in the H-SOD group was −35.6±7.7% and was also significantly suppressed with p<0.003 in comparison with that in the non-treated group as the results of the same statistical test as the above. And since reduction of grip strength in the H-SOD at 1 week and 4 weeks after the initial administration of PC-SOD were significantly suppressed in comparison with that in the L-SOD group (paired Student's t-test. p<0.007 at 1 week, p<0.04 at 4 weeks), it was suggested that PC-SOD suppressed the reduction of grip strength in wobbler mice in a dose dependent manner.

(3) Suppression of decrease in biceps muscle weight

Figure 3:
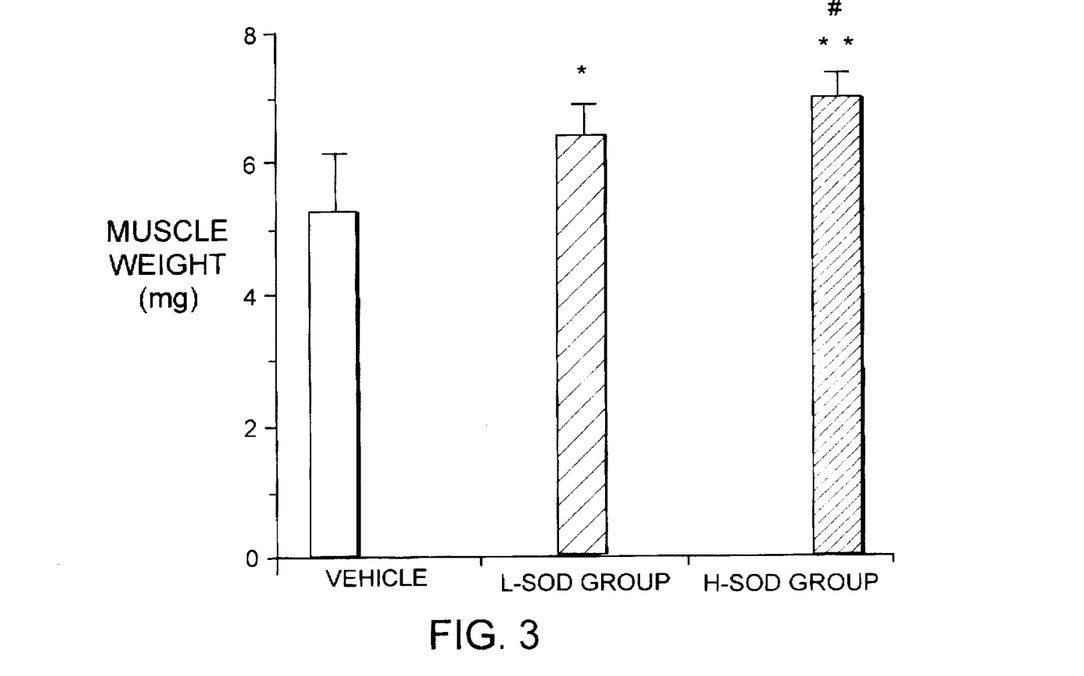
FIG. 3 shows the weight(mg) of biceps muscle at 4 weeks after the initial administration of PC-SOD in the non-treated group, the L-SOD group and the H-SOD group. And, * or ** in the figure means that there was a significant difference with a level of p<0.03 or p<0.001 respectively, compared to the non-treated group. In addition, # means that there was a significant difference with a level of p<0.006 compared to the L-SOD group.

At 4 weeks after the initial administration of PC-SOD, 10 wobbler mice in each group (total 30 mice) and their 5 normal littermates were anesthetized with ether and the right biceps muscle was removed under a dissecting microscope. The biceps muscle was weighed (mean±standard deviation (S.D.) mg) and frozen. The results of determination of biceps muscle weight are shown in FIG. 3.

The average biceps muscle weight of normal littermates was 15.8±0.6 mg. It was concluded that PC-SOD administration significantly increased muscle weight in comparison with non-treatment group as a result of paired Student's t-test (P<0.03 in the L-SOD group and P<0.001 in the II-SOD group). Since the muscle weight in the H-SOD group was significantly heavier than that in the the L-SOD group (P<0.006), it was suggested that PC-SOD suppressed the decrease in biceps muscle weight in a dose dependent manner.

(4) Suppression of the decorate in diameter of biceps muscle fiber

Figure 4:
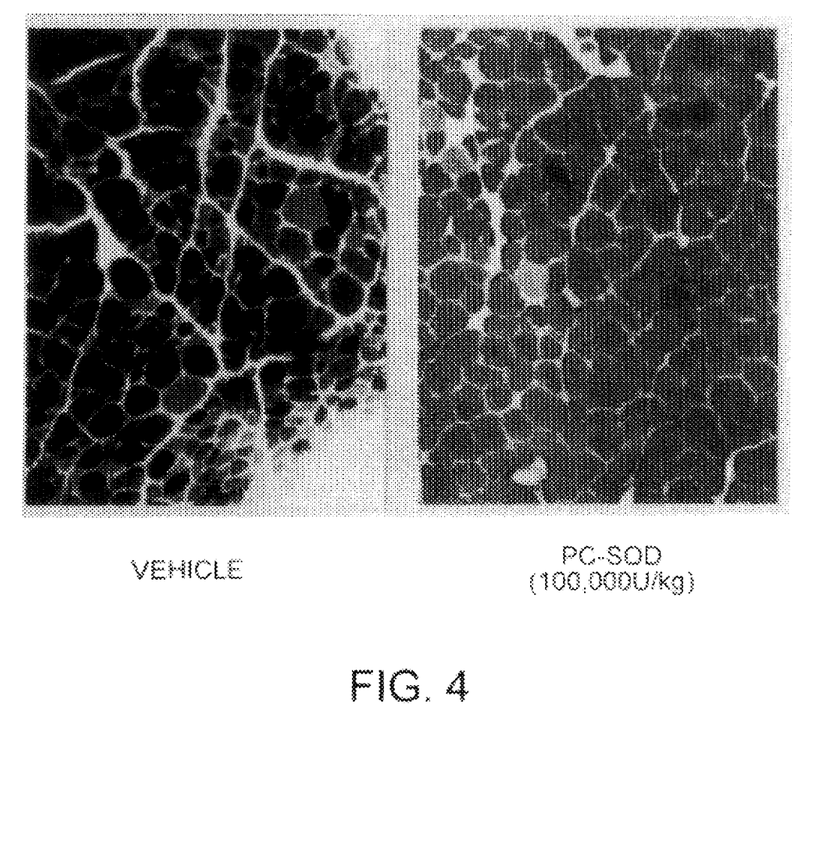
FIG. 4 shows biceps muscle sections stained with ATPase of the non-treated group and the H-SOD group. The magnification was 50 times. (microscopic photograph of tissue of organism)
Figure 5:
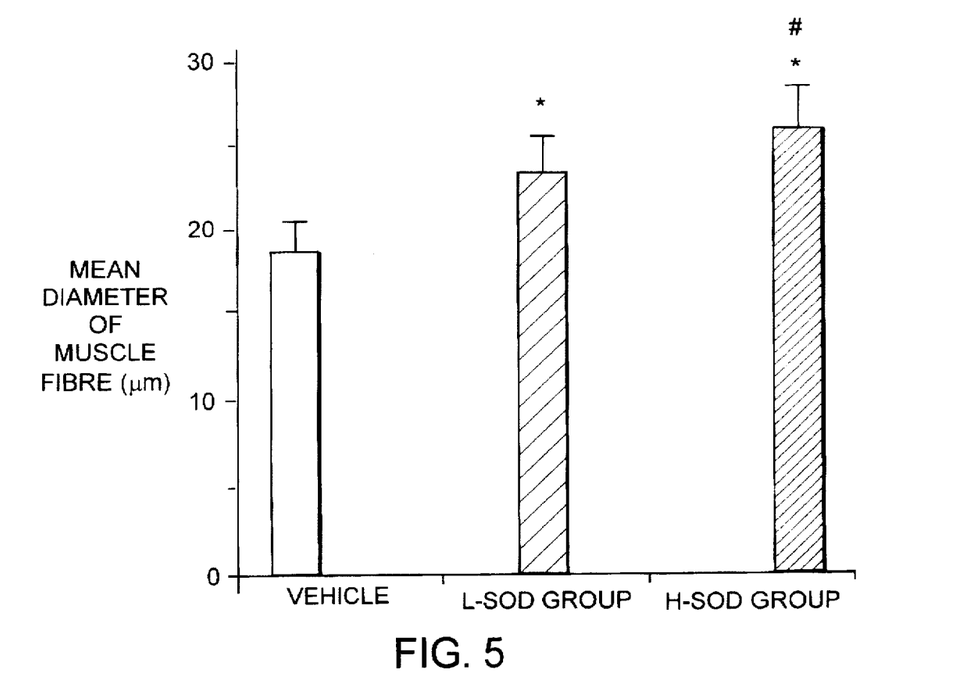
FIG. 5 shows the diameter (μm) of biceps muscle fiber at 4 weeks after the initial administration of PC-SOD in the non-treated group, the L-SOD group and the H-SOD group. And, * in the figure means that there was a significant difference with a level of p<0.001, compared to the non-treated group. Further, # in the figure means that there was a significant difference with a level of p<0.03, compared to the L-SOD group.

Serial 10 µm sections were made from the above frozen biceps muscle and stained with ATPase. To ascertain the correct ATPase fiber types, the soleus and extensor digitorum longue muscle were simultaneously stained. The total number of biceps muscle fibers is approximately 2000, and the majority of fibers were type II fibers. Thus, two areas from the short and long heads of this muscle were arbitrarily selected for histometry. Fifty times magnified histometry of the non-treated group and the H-SOD group are showing inn FIG. 4. This morphometrio analysis revealed that PC-SOD treatment attenuated degeneration muscle atrophy in comparison with non-treatment. The diameter of muscle fibers was determined using a morphometric system, Nikon Cosmozone 1S, and the mean diameter (mean±standard deviation (S.D.) µm) was calculated. Statistical significance was analyzed by paired Student's t-teat. The results are shown in FIG. 5. The mean diameter of biceps muscle fibers of normal littermates was 37.6±0.9 µm. As a result, the diameter of muscle fibers in the L-SOD group and that in the H-GOD group were significantly larger than that in the non-treated group (F<0.001 for the both case). Further, the diameter of muscle fibers that in the H-SOD group was significantly larger than that in the L-SOD group (P<0.03).

From these results, it was suggested that PC-SOD suppressed the decrease of diameter of muscle fibers in a dose dependent manner.

(5) Spinal motoneuron counting

Figure 6:
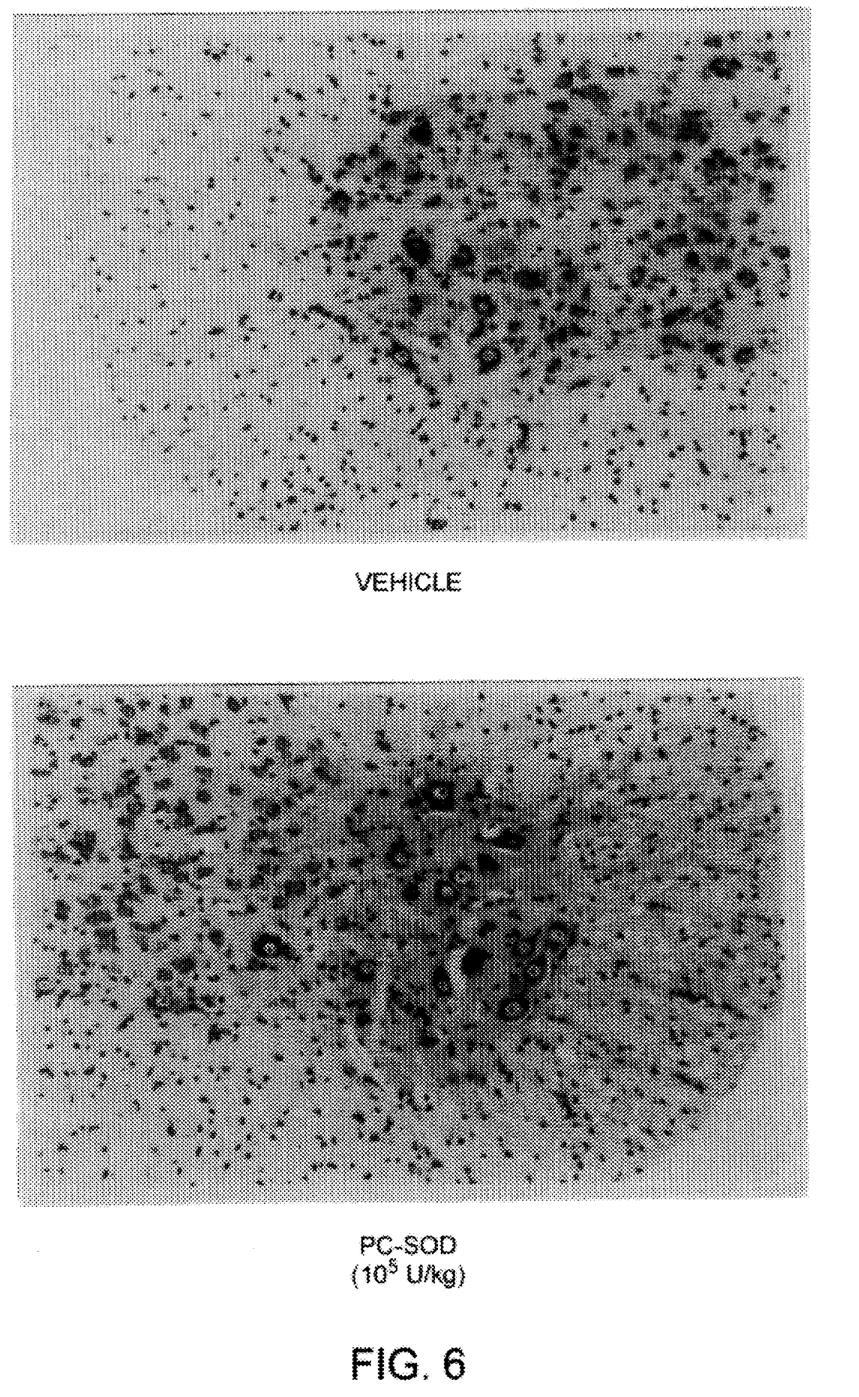
FIG. 6 shows the $C_5$–$C_6$ segments section of spinal cord stained with cresyl-violet in the non-treated group and the H-SOD group. The magnification was 50 times(microscopic photograph of tissue of organism).
Figure 7:
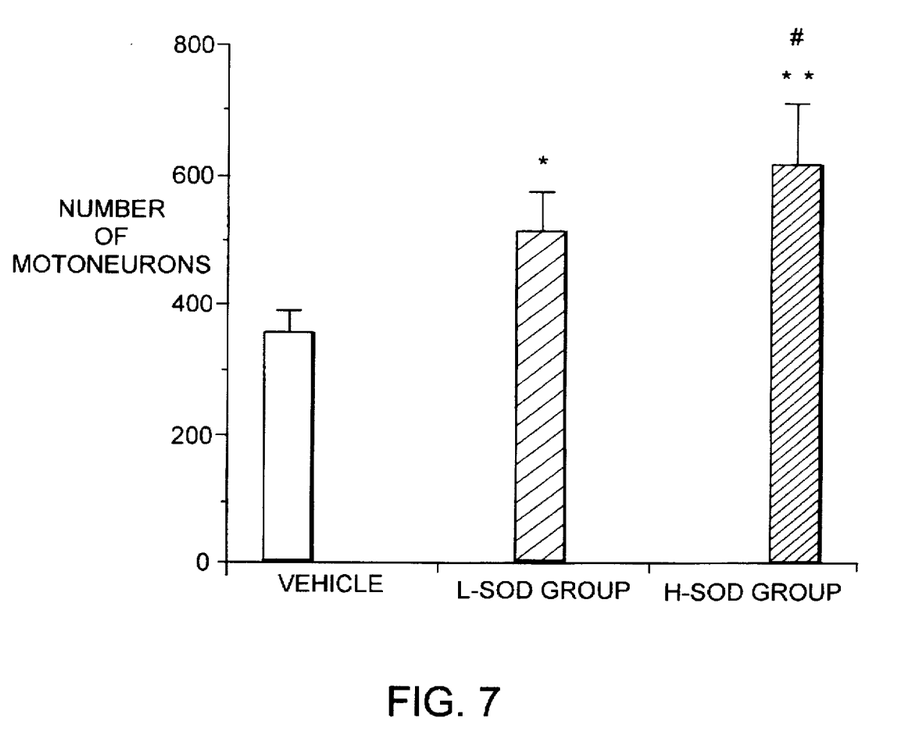
FIG. 7 shows the number of motoneuron of spinal cord at 4 weeks after the initial administration of PC-SOD in the non-treated group, the L-SOD group and the H-SOD group. Further, * or ** means that there was a significant difference with a level of p<0.001 or p<0.0001 respectively, compared to the non-treated group. In addition, # means that there was a significant difference with a level of p<0.02, compared to the L-SOD group.

At 4 weeks after the initial administration of PC-SOD, 10 wobbler mice in each group(total 30 mice) and their 5 normal littermates were anesthetized with ether and perfused through an intracardiac catheter with phosphate buffered saline(PBS) followed by 4% paraformaldehyde, 1% glutaraldehyde, 0.1M sodium phosphate buffer (pH 7.4). Laminectomy was performed, and the cervical spinal cords war removed under a dissecting microscope. For motoneuron counting, the $C_5$–$C_6$ segments which innervate the biceps muscle were token for analysis, because prominent degeneration occurs at the $C_5$–$C_6$ segments in wobbler mice. The spinal cord segments were embedded in paraffin, sectioned serially at 10 µm in the transverse plain, and stained with cresyl-violet. Fifty times magnified histometory is shown in FIG. 6, which revealed that the degeneration in the H-SOD group was retarded in comparison with that in the non-treated group. Further, to exclude small interneurons in the view horn of spinal cord, large motoneurons (larger than 20 µm) with prominent nucleoli were counted at every 5th section under 200× magnification by two investigators (blind as to treatment). The number of large motoneuron (mean±S.D.) was determined. The statistical significance was analyzed by paired Student's t-test. The results are shown in FIG. 7. The mean number of motoneurons of normal littermates was 1201.3±113.8. From this result, the number of motoneurons in the L-SOD group and that in the H-SOD group were significantly larger than that in the non-treated group (P<0.001 in the L-SOD group and P<0.0001 in the H-SOD group). Further, the member of motoneurons in the H-SOD group was significantly larger than that in the L-SOD group (P<0.02), which suggested that PC-SOD increased the number of motoneurons in a dose dependent manner. Therefore, it was suggested that PC-SOD suppressed the decrease in the number of spinal motoneurons in a dose dependent manner.

Comparative Example

In replace of the Dave PC-SOD, non-lecithinized human Cu/Zn SOD derivative (hereinafter abbreviated as "free SOD") prepared in the preparation example <1> was used in the same experiment as described in the aforementioned pharmacological tests (1)–(3), and (5) in order to investigate the below items (1)–(4).

The final concentration of 5 mg/ml of free SOD dissolved in 5% mannitol aqueous solution was used and the dosage of intraperitoneal administration were the same as in the aforementioned example, comprising a group administered $10_4$ U/kg (hereinafter abbreviated as LF-SOD group) and a group administered $10_5$ U/kg (hereinafter, abbreviated as HF-SOD group).

(1) Progression of deformity of forelimb

The grade of forelimb deformity in wobbler mice at 4 weeks after the initial administration of from SOD was scored as described above. The results are shown below. "n" represents the number of mice and the value represents the rate of mice in each deformity grade to all mice in each group:

LF-SOD group(n=10): grade 1 20%
  grade 2 40%
  grade 3 20%
  grade 4 20%
HF-SOD group(n=8) grade 1 12.5%
  grade 2 25%
  grade 3 37.5%
  grade 4 25%

It was clear from the results that neither of LF-SOD group or HF-SOD group suppressed the progression of deformity as seen in the case of tho PC-SOD administration.

(2) Reduction of grip strength

The results of the determination of grip strength of mice relieved free SOD at 4 weeks after the initial administration are shown as follows, wherein n represents the number of mice and grip strength was represented as mean values± standard deviation (S.D.):

LF-SOD group (n=10): 4.8+4.9 g

HF-SOD group (n=10): 6.7+6.3 g

As it was clear from the results, neither of LF-SOD group nor the HF-SOD group showed suppressive effect on the reduction of grip strength as seen in the case of PC-SOD administration.

(3) Decrease of the biceps muscle weight

The results of the determination of biceps muscle weight of mice received free SOD at 4 weeks after the initial administration are shown as follows, wherein n represents the number of mice and biceps muscle weight was represented as mean value+standard deviation (S.D.):

LF-SOD group (n=10): 4.93+0.82 mg

HF-SOD group (n=10): 4.93+0.93 mg

As it was clear from the results, neither of the LF-SOD group nor HF-SOD group showed suppressive effect on the decrease of biceps muscle weight as seen in the case of PC-SOD administration.

(4) Spinal motoneuron containing

The results of the spinal motoneuron counting in mice recieved free SOD at 4 weeks after the initial administration are shown as follows, wherein n represents the number of mice and the number of motoneurons was represented as mean value±standard deviation (.S.D.):

LF-SOD group (n=3): 306.6+15.3

HF-SOD group (n=8): 298.0+131.9

As it was clear from the results, neither of the LF-SOD group nor HF-SOD group showed suppressive effect on the decrease of the number of motoneurons as seen in the case of PC-SOD administration.

From the results of the aforementioned examples and the comparative examples, it wag confirmed that PC-SOD had an improving action on motoneuron-dosieases as not seen in the case of free SOD.

EXAMPLE 2
Pharmaceutical Preparation Example (1) Injections

PC-SOD prepared in the aforementioned preparation example (30 mg/ml) was dissolved in 5% mannitol to the final concentration of 5 mg/ml, followed by sterilization by filtration, dispensed in 2 ml aliquots into ampules and sealed.

(2) Tablets

One hundred mg lyophilized PC-SOD prepared in the aforementioned preparation example, 670 mg of lactose, 150 mg of potato starch, 60 mg of crystalline cellulose and 50 mg of light silicic acid anhydride wear mixed, to which 30 mg of hydroxypropylcellulose dissolved in methanol (10 weight % of hydroxypropylcellulose solution) was added and mixed, followed by granulation, extrusion with a 0.8 mm diameter screen to make granules, drying and adding 15 mg of magnesium stearate to make 200 mg tablet.

(3) Capsules

One hundred mg of lyophilized PC-SOD prepared in the mentioned preparation example, 150 mg of potato starch, 50 mg of light silicic acid anhydride, 10 mg of magnesium stearate and 765 mg of lactose were homogeneously mixed and 200 mg of the mixture was taken and packed in each hard capsules.

We claim:

1. A method for treating motoneuron disease in mammals which comprises administrating to a mammal in need of such treatment a therapeutically effective dosage of a superoxide dismutase conjugated to lecithin through chemical crosslinking.

2. The method according to claim 1 wherein said superoxide dismutase conjugated to lecithin through chemical crosslinking is represented by the following formula (1):

wherein,

SOD is superoxide dismutase;

X is a lysolecithin residue represented by the following formula (2):

wherein R in formula (2) is an acyl group;

m is an average integral number to of between about 1 to about 16 and n is an integral number between about 2 to about 10".

3. The method according to claim 2, wherein R in the formula (2) is a saturated or unsaturated acyl group with 10 to 28 carbon atoms.

4. The method according to claim 2, wherein R in the formula (2) is a saturated acyl group with 14 to 22 carbon atoms.

5. The method according to claim 2, wherein R in the formula (2) is palmitoyl group.

6. The method according to any one of claims 2 to 5, wherein said SOD is a human superoxide dismutase coordinated with Cu and Zn whose amino acid at position 111 is S-(2-hydroxyethylthio)cystein.

7. The method according to claim 2, wherein n in formula (1) is 3.

8. The method according to claim 2, wherein m in formula (1) is 4.

9. The method according to any one of claims 1 to 5, wherein said motoneuron disease is amyotrophic lateral sclerosis.

10. A method for treating motoneuron disease in mammals which comprises administering to a mammal in need of such treatment a therapeutically effective dosage of a superoxide dismutase conjugated to lecithin through chemical crosslinking, wherein said therapeutically effective dosage is at least about 100 units per kilogram.

11. The method according to claim 10 wherein said superoxide dismutase conjugated to lecithin through chemical crosslinking is represented by the following formula (1):

wherein,

SOD is superoxide dismutase

X is a residue of lysolecithin represented by the following formula (2):

wherein R in formula (2) is an acyl group;

m is an average integral number to of between about 1 to about 16 and n is an integral number between about 2 to about 10".

12. The method according to claim 11, wherein R in formula (2) is a saturated or unsaturated acyl group comprising from about 10 to about 28 carbon atoms.

13. The method according to claim 11, wherein R in formula (2) is a saturated acyl group comprising from about 14 to about 22 carbon atoms.

14. The method according to claim 11, wherein R in formula (2) is a palmitoyl group.

15. The method according to any one of claims 11 to 14, wherein said SOD is a human superoxide dismutase coordinated with Cu and Zn having an amino acid at position 111 comprising S-(2-hydroxyethylthio)cysteine.

16. The method according to claim 11, wherein n in formula (1) is 3.

17. The method according to claim 11, wherein m in the formula (1) is 4.

18. The method according to any one of claims 10 to 14, wherein said motoneuron disease is amyotrophic lateral sclerosis.

* * * * *